United States Patent [19]
Honda et al.

[11] Patent Number: 5,295,325
[45] Date of Patent: Mar. 22, 1994

[54] PLANT CUTTING AND TRANSPLANTING APPARATUS FOR CULTURING A PLANT TISSUE

[75] Inventors: Shigeru Honda; Masahiro Sei; Hitoshi Uemura; Tatsuya Mori; Chikaya Sakai; Ruriko Oda; Chiyoko Shimada; Yusaku Sekino, all of Kanagawa, Japan

[73] Assignee: Kabushiki Kaisha Komatsu Seisakusho, Tokyo, Japan

[21] Appl. No.: 640,705

[22] Filed: Jan. 14, 1991

[51] Int. Cl.$^5$ .............................................. A01G 7/00
[52] U.S. Cl. ...................................................... 47/1.01
[58] Field of Search ............................ 47/901, 1 A, 1.01

[56] References Cited

U.S. PATENT DOCUMENTS

| | | | |
|---|---|---|---|
| 2,069,958 | 2/1937 | Kool | 47/1.01 |
| 2,771,709 | 11/1956 | Ritter | 47/901 |
| 5,131,185 | 7/1992 | Wingerden | 47/901 |

FOREIGN PATENT DOCUMENTS

| | | | |
|---|---|---|---|
| 2607657 | 6/1988 | France | 47/1.01 |
| 2615066 | 11/1988 | France | 47/1 R |
| 1-273517 | 11/1989 | Japan . | |
| 2-76519 | 3/1990 | Japan . | |
| 2-190118 | 7/1990 | Japan . | |
| 2-211810 | 8/1990 | Japan . | |
| 9101628 | 2/1991 | Netherlands | 47/1.01 |

*Primary Examiner*—Ramon S. Britts
*Assistant Examiner*—Joanne C. Downs
*Attorney, Agent, or Firm*—Frost & Jacobs

[57] ABSTRACT

A plant cutting and transplanting apparatus comprises a plant cutting/transplantation room accommodating a first culture box in which multiplied plants to be cut are planted, and a second culture box in which nodular pieces made by cutting the plants are transplanted; a cutting device adapted to cut, in one lot, the plants in the first culture box to the form of nodular pieces and configured to allow the nodular pieces to rest on the edges thereof, the cutting device being arranged so as to be moved vertically and transversely above the space where the first and second culture boxes are placed; and a blade device having a blade for shaking down the nodular pieces which rest on the cutter and which have been moved to a position above the second culture box. The apparatus further comprises nozzle device for spraying a cleaning liquid to sterilize the cutting and transplanting room; tanks each containing a liquid sterilizing agent and an aseptic liquid; a machine room located above the cutting and transplantation room; driver means for driving the cutting device and the blade device; supporting means connected to the drivers and supporting the cutter and the blade; and a filter for supplying sterile air into the cutting/transplantation room to keep the room in an aseptic condition.

8 Claims, 4 Drawing Sheets

PLANT CUTTING AND TRANSPLANTING APPARATUS FOR CULTURING A PLANT TISSUE

BACKGROUND OF THE INVENTION

1. Field of the Invention

This invention relates to a plant cutting and transplanting apparatus for culturing a plant tissue.

2. Description of the Prior Art

Prior art plant tissue culturing apparatuses require operations of manually cutting plants by means of razors or surgical knives to individual nodular pieces to be cultured in a clean bench or the like, and then transplanting the nodular pieces in culture ground.

Further, as an apparatus for automatically conducting the above-mentioned operations, a robot adapted to hold an edged tool such as scissors by a manipulator and cut plants into nodular pieces one by one while sensing their positions is under development stage aiming at its practical use.

In the former prior art apparatus, in case a great many nodular pieces, for example, several ten thousand pieces per day, were made by cutting plants, and then transplanted, a large number of workers were required. Whilst, in the latter prior art apparatus using the robot, in case 50,000 nodular pieces are made by cutting plants for eight hours a day, it is necessary to make and transplant one nodular piece for about 0.6 seconds. Such processing speed is difficult to be attained, and further difficulties are encountered in sterilizing the robot itself initially and maintaining a sterile condition in surrounding environment.

SUMMARY OF THE INVENTION

The present invention has been devised in view of the above-mentioned circumstances in the prior art and has for its object to provide a plant cutting and transplanting apparatus for culturing a plant tissue, which is capable of treating a multiplicity of nodular pieces efficiently by means of a comparatively simple construction in case cutting and transplantation of plants for multiplying in an aseptic condition the plants which have been cultured in an aseptic condition are conducted.

To achieve the above-mentioned object, according to a first aspect of the present invention, there is provided a plant cutting and transplanting apparatus for culturing a plant tissue, comprising: a plant cutting and transplantation room accommodating in a spaced-apart relationship a first culture box in which a group of multiplied plants to be cut are planted, and a second culture box in which nodular pieces made by cutting the plants are transplanted; a cutting device having a cutter adapted to cut, in one lot, the group of the plants planted in the first culture box to the form of individual nodular pieces and configured to allow the nodular pieces to rest on the upper surfaces of the edges thereof, the cutting device being provided in the plant cutting and transplantation room in such a way as to be moved vertically and transversely above the space where both the first and second culture boxes are accommodated; and a blade device having a blade adapted to shake down the nodular pieces which rest on the edges of the cutter and which have been carried to a position above the second culture box for transplantation purposes.

According to a second aspect of the present invention, there is provided a plant cutting and transplanting apparatus for culturing a plant tissue as set forth in the above-mentioned first aspect, further comprising: nozzle device provided in the plant cutting and transplantation room so as to spray a cleaning liquid for conducting the cutting of the plants in an aseptic condition; and a tank containing a liquid sterilizing agent and a tank containing an aseptic liquid, both of which are connected through a hydraulic pump and a change-over valve to the nozzle device.

According to a third aspect of the present invention, there is provided a plant cutting and transplanting apparatus for culturing a plant tissue as set forth in the above-mentioned first aspect, further comprising: a machine room located above the plant cutting and transplantation room and separated by a partition ceiling from the same; driver means installed in the machine room and adapted to drive the cutting device and the blade device; and supporting means connected to the driver means, respectively, and extending through the partition ceiling so as to support the cutter and the blade.

According to a fourth aspect of the present invention, there is provided a plant cutting and transplanting apparatus for culturing a plant tissue as set forth in the above-mentioned third aspect, characterized in that the plant cutting and transplantation room is maintained in an aseptic condition with sterile air kept at a positive pressure by ventilating air through a filter provided on the partition ceiling through the intermediary of a sealing member.

According to a fifth aspect of the present invention, there is provided a plant cutting and transplanting apparatus for culturing a plant tissue as set forth in the above-mentioned third aspect, characterized in that the blade is connected through the intermediary of a cushion member to the supporting means.

The operation of the plant cutting and transplanting apparatus according to the present invention incorporating the above-mentioned aspects is as follows.

A number of multiplied plants planted in the first culture box which is accommodated in the plant cutting and transplantation room are cut in one lot by the cutter of the cutting device to individual nodular pieces each having a predetermined length, and placed on the upper surfaces of the edges of the cutter, and then transferred by the cutting device to a position above the second culture box for transplantation purposes. At that time, the blade of the blade device located above the cutter is moved transversely together with the cutter in synchronism therewith. When both the cutter and the blade have been moved to the position above the second culture box for transplantation purposes, the blade is lowered to such a position as to contact the nodular pieces of the plants resting on the cutter, and then only the cutter is moved transversely away from the blade so that the nodular pieces resting on the cutter are shaken down by the blade into the second culture box for transplantation purposes.

By conducting the above-mentioned operations repeatedly, the multiplied plants planted in the first culture box for cutting purposes are cut in turn to nodular pieces each having a predetermined length, and then transplanted in the second culture box for transplantation purposes. And, the second culture box in which the nodular pieces have been transplanted is taken out of the plant cutting and transplantation room, and then a new box is carried into the room.

The plant cutting and transplantation room is sterilized with a liquid sterilizing agent sprayed through the nozzles. It is of course possible to sterilize the room with a gas such as EOG.

According to the present invention, in the process of cutting and transplanting in an aspetic condition the plants which have been cultured in a sterile condition, a multiplicity of nodular pieces made by cutting the plants can be treated efficiently by an apparatus having a simple construction.

The above-mentioned and other objects, aspects and advantages of the present invention will become apparent to those skilled in the art by making reference to the following detailed description and the accompanying drawings in which a preferred embodiment incorporating the principles of the present invention is shown by way of example only.

DETAILED DESCRIPTION OF THE PREFERRED EMBODIMENT

The present invention will now be described in detail below by way of a preferred embodiment thereof with reference to the accompanying drawings.

Figure 1:
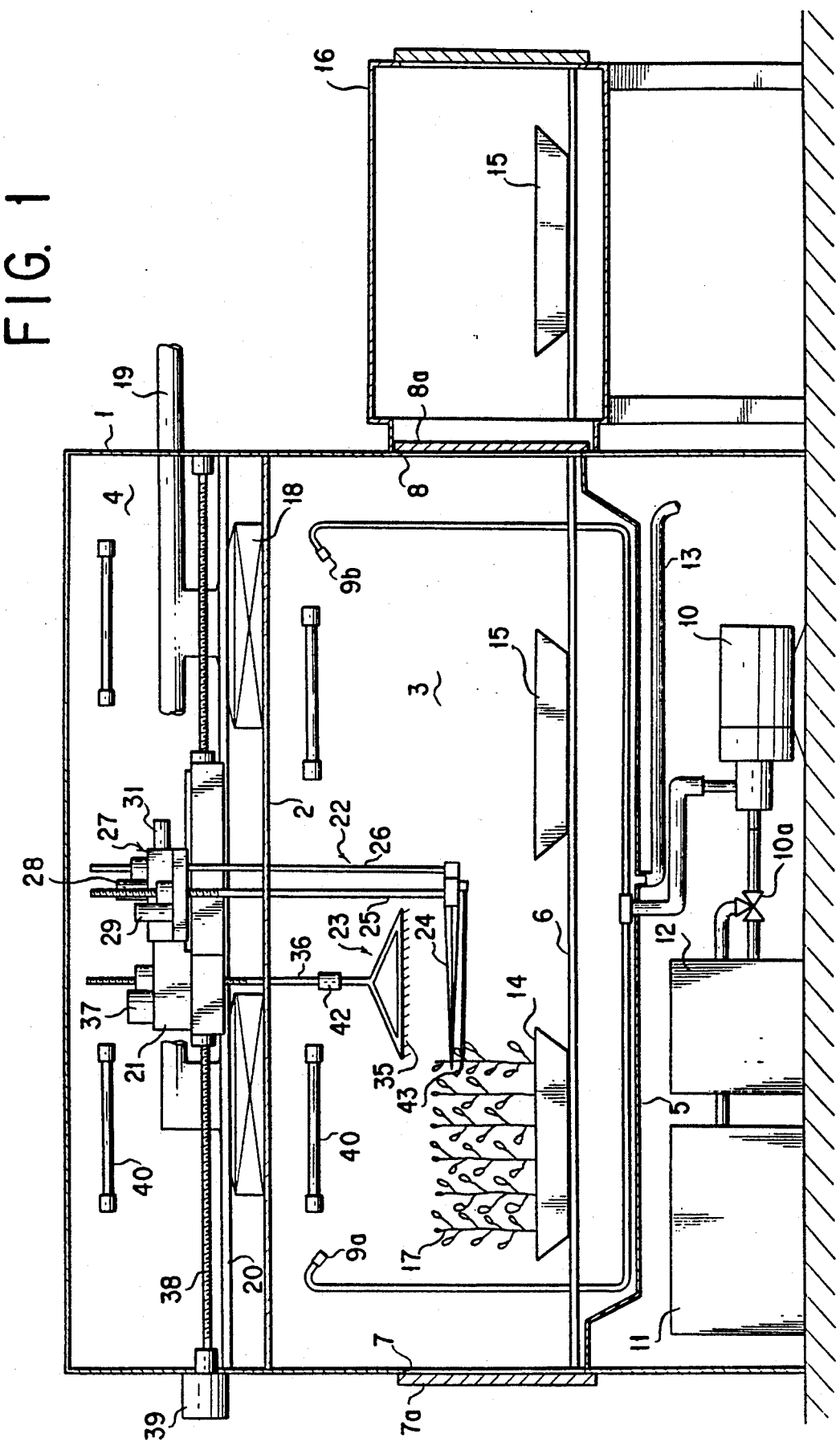
FIG. 1 is an overall, schematic explanatory view showing the construction of one embodiment of the present invention.

In FIG. 1, reference numeral 1 denotes a bench which is divided by a partition ceiling 2 into an upper room, i.e., a machine room 4, and a lower room, i.e., a plant cutting and transplantation room 3. The plant cutting and transplantation room 3 is provided with a pallet 5 at its bottom. Located above the pallet 5 is a rail which extends transversely across the plant cutting and transplantation room 3. Further, the plant cutting and transplantation room 3 is provided with doorways 7 and 8. The doorways 7 and 8 are fitted with doors 7a and 8a, respectively, which can be opened and shut hermetically. Cleaning agent spraying nozzles 9a and 9b are installed inside the plant cutting and transplantation room 3. These nozzles 9a and 9b are connected to a hydraulic pump 10 installed outside of the plant cutting and transplantation room 3. Further, the hydraulic pump 10 is connected by way of a three-way valve 10a to a liquid sterilizing agent tank 11 and a sterile liquid tank 12, respectively. The pallet 5 has a drainage pipe 13 connected thereto.

Reference numeral 14 denotes a first culture box in which a group of multiplied plants to be cut are planted, and 15 a second culture box in which nodular pieces obtained by cutting the group of the plants are transplanted. These culture boxes 14 and 15 are placed on the above-mentioned rail 6. The first culture box 14 is taken in and out through the left-hand doorway 7, whilst the second culture box 15 is taken in and out through the right-hand doorway 8. Further, the right-hand doorway 8 is connected to a sterile operation room 16. Reference numeral 17 denotes a plant such as, for example, carnation planted in the above-mentioned first culture box 14.

The above-mentioned partition ceiling 2 is provided with a filter 18 which is oriented to the cutting and transplantation room 13 and which is connected to an air duct 19 so as to fill the room 13 with sterile air kept at a positive pressure.

Installed inside of the machine room 4 is a transversely extending rail 20, on which a trailer 21 is located in such a way as to be moved freely in the transverse direction. The trailer 21 is provided with a cutting device 22 and a blade device 23.

The above-mentioned cutting device 2 is located inside the plant cutting and transplantation room 3, and comprises a hair-cutting shaped cutter 24 located opposite to a number of multiplied plants 17 to be cut which are planted in the first culture box 14, a supporting rod 25 for supporting the cutter 24, a driving/supporting rod 26 for driving and supporting the cutter 24, and a driving device 27 resting on the trailer 21. The above-mentioned driving rod 26 is rotated by a cutter driving motor 28 of the driving device 27 and supported in such a way as to be moved freely in the vertical direction. Further, the upper portion of the supporting rod 25 is constituted by a screw-threaded portion. This screw-threaded portion is threadably engaged with a nut member (not shown) connected to a motor 29 of the driving device 27 for vertical movement. The arrangement is made such that rotation of the nut member causes the cutting device 22 to be moved up or down. Further, the above-mentioned driving device 27 is arranged to be moved transversely by a feed motor 31 relation to the above-mentioned trailer 21.

Figure 2A:
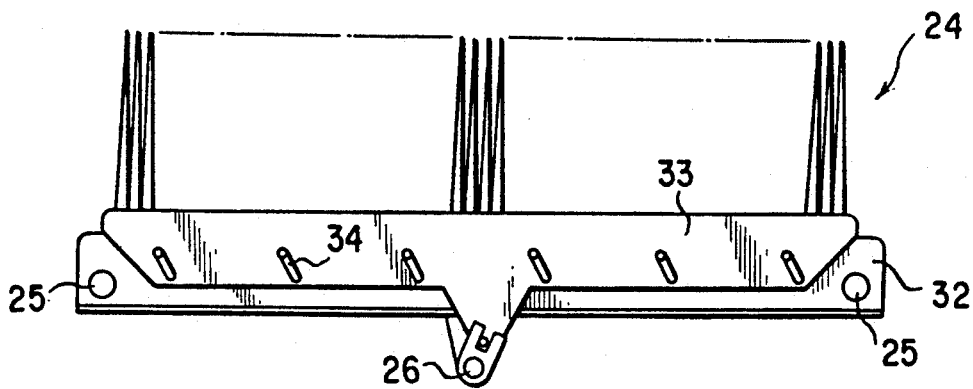
FIGS. 2A and 2B are a plan view and a sectional view showing the construction of a cutter.
Figure 2B:
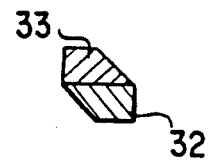

As shown in FIGS. 2(A) and 2(B), the cutter 24 comprises a comblike stationary edge 32 (lower portion) and a movable edge 33 (upper portion). The arrangement is made such that as the driving rod 26 is rotated the movable edge 33 is reciprocated along cutter guides 34 fixedly secured to the stationary edge 32.

The stationary edge 32 and the movable edge 33 are laid to overlap each other as shown in FIG. 2(B) so as not to expose their sharp portions so that when they are inserted through the group of the plants 17. Further, after completion of cutting the plants 17, the edges 32 and 33 are laid one on top of another or more or less out of phase, as shown in FIG. 2(A).

The blade device 23 is comprised of a blade 35 located above the cutter 23, and a rod 36 for supporting the blade 35. This blade supporting rod 36 is supported by the trailer 21 so as to be moved vertically, but without rotation. And, the upper portion of the blade supporting rod 36 is formed by a screw-threaded portion. This screw-threaded portion is threadably engaged with a nut member (not shown) which is rotated by a motor 37 mounted on the trailer 21 for the purpose of moving the blade 35 up and down.

The above-mentioned trailer 21 is threadably engaged with and supported by a transversely extending feed screw 38 installed in the machine room 4. The arrangement is made such that the trailer 21 is moved to the left or to the right when the feed screw 38 is rotated by a feed motor 38 clockwise or counterclockwise.

The rods 25 and 26 of the cutting device 22 and the rod 36 of the blade apparatus 23 pass through the above-mentioned partition ceiling 2 where notches (not shown) are provided to allow movement of the rods 25, 26 and 36. These notches are closed by resilient sealing members. The arrangement is made such that the above-mentioned rods 25, 26 and 36 are moved while pushing open their respective sealing members.

In each of the plant cutting and transplantation room 3 and the machine room 4, sterilizing ultra-violet lamps 40 are provided which serve to sterilize the interior of these rooms when the culture boxes are put out of the room 3, i.e., the operation is suspended, for example, during night.

The plant tissue cutting and transplanting operation by means of the above-mentioned cutting and transplanting apparatus will be described below.

In the first place, a liquid sterilizing agent, such as, for example, gultaric aldehyde liquid is sprayed through the nozzles 9a and 9b into the hermetically sealed cutting and transplantation room 3 thereby sterilizing the interior thereof. After that, the three-way valve 10a is switched over so as to spray sterile water stored in the sterile water tank 12 through the nozzles 9a, 9b into the room 3 thereby washing away the sterilizing agent. These liquids are drained from the pallet 5 through the drainage pipe 13.

After that, the first culture box 14 in which a group of multiplied plants to be cut are planted is carried from the left-hand doorway 7 along the rail 6 into the cutting and transplantation room 3 which have been sterilized as mentioned above. Further, the second culture box 15 for transplantation purpose is carried from the right-hand doorway 8 along the rail 6. Multiplied plants 17 (for example, carnations) are planted thick in the soil in the above-mentioned first culture box 14.

In the next place, the trailer 21 provided in the machine room 4 is moved along the rail 20 so as to move the cutting device 22 to the left or to the right, and then the cutting device 22 is moved up or down so as to locate the cutter 24 opposite to the plants 17 planted in the first culture box 14. At that time, the blade device 23 is located above the cutter 24.

Figure 3:
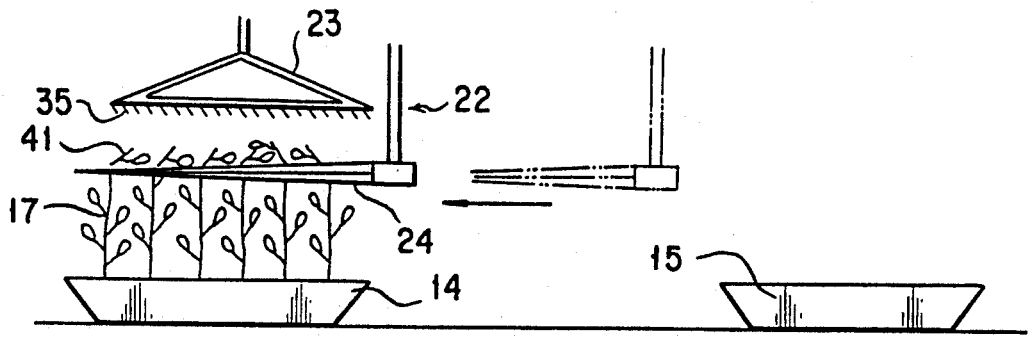
FIGS. 3, 4 and 5 are explanatory views showing the operations of the cutter and the blade, respectively.

The cutting device in such a condition is advanced by the trailer 21 towards the first culture box 14 so as to introduce the cutter 24 into the group of the plants 17 thereby cutting them, at a position lower than their uppermost ends thereof by a predetermined distance, for example 10 mm, to the form of individual nodular pieces 41. At that time, the nodular pieces 41 remain placed on the cutter 24 (FIG. 3). AT that time, a growth promotion agent such as, for example, a vegetable hormone may be sprayed onto the nodular pieces 41.

Figure 4:
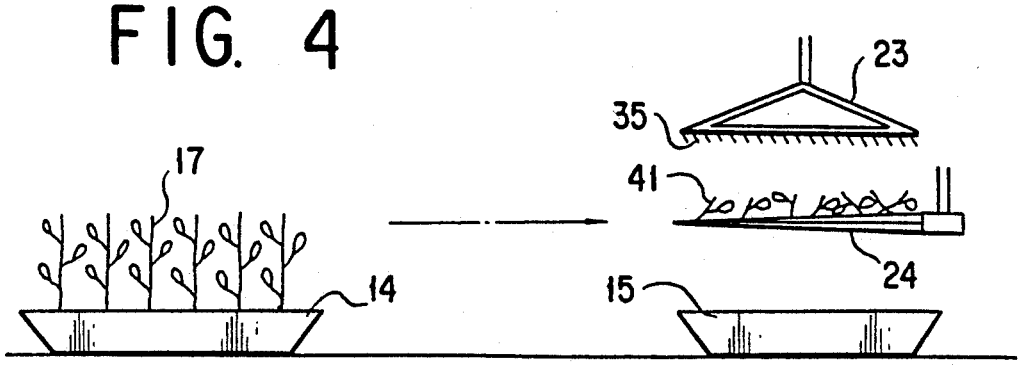

After completion of the plants 17 at the first step, the cutting device 22 is moved transversely by the trailer 21 along the rail 20 to a position above the second culture box 15 for transplantation purposes. At that time, the blade device 23 is also moved together with the cutting device 22. (FIG. 4)

Figure 5:
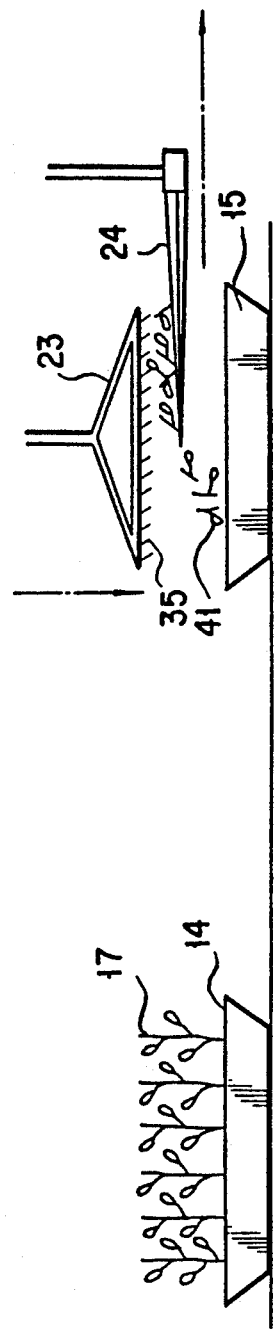

Subsequently, the blade 35 of the blade device 23 is moved down and stopped at a position where it pushes down lightly the nodular pieces 41 which rest on the cutter 24. After that, only the cutting device 22 is moved relative to the trailer 21 and away from the blade device 23. By so doing, the cutter 24 is withdrawn away from the blade 35, so that the nodular pieces 41 which rest on the cutter 24 are shaken down by the blade 35 into the second culture box 15 for transplantation purposes. Since the above-mentioned nodular pieces 41 are shaken down sequentially with the movement of the cutter 24, the nodular pieces 41 which have been dropped are transplanted in the soil in the second culture box 15 in the same positional relationship as that on the cutter 24 as shown in FIG. 5. Further, at that time, the cutter 24 is set at a proper height relative to the second culture box 15 for transplantation purposes.

Upon completion of the above-mentioned operation, the cutting device 21 is moved back to its original position relative to the trailer 21, and then the trailer 21 is moved to the left while the blade 35 is moved upwards so as to locate the cutter 24 again opposite to the plants 17 in the first culture box 14 thereby cutting the plants 17, at a position lower than their uppermost ends by 10 mm, to the form of nodular pieces. After that, the above-mentioned operation is carried out repeatedly.

The second culture box 15 in which a group of nodular pieces 41 have been transplanted is taken out from the cutting and transplantation room 13 each time the transplantation is completed, and carried in another culture room. After that, a new second culture box 15 for transplantation purposes is carried into the cutting and transplantation room 3.

In the above-mentioned operation, the cutter 24 of the cutting device 22 is moved down by a distance equivalent to the length of each of the nodular pieces 41 each time one cutting cycle is completed, and the pitch of downward movement is adjusted to the desired length of each of the nodular pieces 41.

The length of each of the nodular pieces 41 should desirably be set at such a value as each piece has its node located on the intermediate portion thereof.

Figure 6:
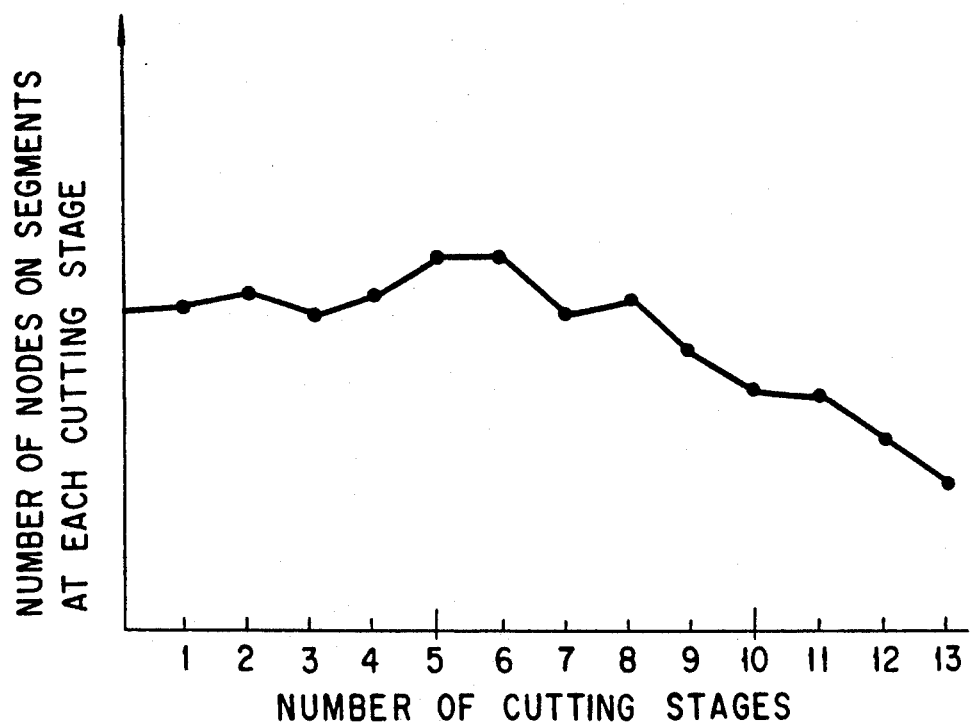
FIG. 6 is a graph showing the number of nodes on segments of plants at each cutting stage obtained by cutting each of the plants from its lowermost end to the top thereof into a plurality of stages each having a length of 10 mm.

FIG. 6 is a graph showing the number of nodes on segments of plants 17 at each cutting stage obtained by cutting each of the plants 17 from its lowermost end to the top thereof into a plurality of stages each having a length of 10 mm, and the axis of abscissas shows the number of cutting stages, whilst the axis of ordinates shows the number of nodes on segments at each cutting stage.

In case the plants are cut at a certain pitch, there is a possibility of some pieces having no node. Therefore, the optimum pitch in terms of the unit of millimeter to be selected to enhance the yield can be obtained by using the above-mentioned data. However, the plant cutting and transplanting apparatus according to the present invention is not intended to be restricted to how to decide the number of nodular pieces and the pitch at which the plants are to be cut, using the above-mentioned data.

Further, when the cutting and transplanting apparatus is not in operation, the sterilizing ultra-violet lamps 40 are turned on and ventilation of air through the filter 18 is made. Further, at that time, the cutting and transplantation room 3 is always kept at a positive pressure and in a sterile condition by sending sterilized air through the air duct 19 and the filter 18.

Further, in the above-mentioned embodiment, it is possible to move the trailer 21 by meshing a rack provided on the rail 20 with a pinion provided on the side of the trailer 21 instead of using the feed screw 38.

Further, by connecting the blade 35 of the blade device 23 to the supporting rod 36 by means of a cushion members 42, it becomes possible for the blade 35 to hold down the nodular pieces 41 which are placed on the cutter 24 without transmitting any shock to the blade 35. Further, the blade 35 is fitted with a silicone rubber configured to have a shape corresponding to the arrangement of the edges of the cutter 24 for the purpose of shaping down the nodular pieces 41 without giving damage to them.

As the motor 29 for moving the cutter 24 up and down and the feed motor 39 for moving the trailer 21 transversely, stepping motors are used. The purpose of using the stepping motors is to enable the height of the plant stem from the root thereof to be cut off and the horizontal position of the cutter 24 to be set or selected as will. This is because if the arrangement is made to stop the cutter 24 by means of a sensor, it becomes necessary to sterilize the sensor depending on the position of the sensor thus rendering the configuration complicated, or rendering the control difficult.

In the above-mentioned embodiment, the position of the cutter 24 and that of the blade 35 are controlled, as desired, using only the reference point sensor for vertical movement purposes and a reference point sensor for transverse feed purposes. Further, AC motors or DC motors may be used instead. In this case, a sensor 43 is provided to detect the position of the first culture box 14 in which a group of multiplied plants to be cut are planted. This sensor 43 is formed in a construction capable of resisting sterilization by embedding a photosensor in a glass tube such as, for example, a test tube and passing electrical wires through a silicone tube.

Figure 7:
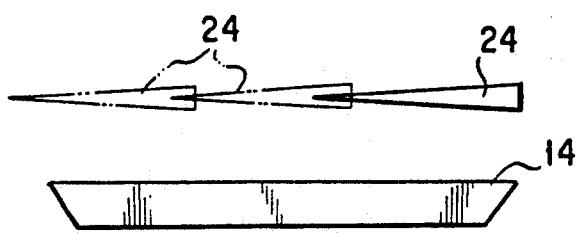
FIG. 7 is an explanatory view showing the operating condition of the cutter relative to a first culture box in which a group of multiplied plants to be cut are planted.

Since the whole of the cutter 24 needs to be sterilized, the cutter 24 may be made of an anti-corrosion and chemical attack resisting material such as stainless steel, ceramic or the like. In the embodiment of the present invention, zircon or ceramic is used to form the cutter 24. Further, the length of the cutter 24 cannot be made identical to that of the first culture box 14 from the manufacturing point of view, however, it is necessary to shift the cutter 24 transversely, as shown in FIG. 7. Furthermore, when the cutter 24 is inserted through the group of thick plants 17, there is a possibility of the plants 17 being pushed down by the edge of the cutter depending on the configuration of the edge and the thick grown condition of the plants 17. In such a case, it is possible to prevent the plants 17 from falling down by moving the center 24 forward by a predetermined stroke moving it back a little. As an alternative, the cutter 24 may be inserted into the group of the plants while swinging it vertically. By so doing, it is ensured that nodes and leaves of the plants present on the stems from the roots to the leading ends are located in the length of each of the nodular pieces. Further, to prevent the plants from being pushed down by the edge of the cutter, the above-mentioned two methods may be used in combination.

It is to be understood that the foregoing description is merely illustrative of a preferred embodiment of the present invention, and that the scope of the present invention is not to be limited thereto, but is to be determined by the scope of the appended claims.

What is claimed is:

1. A plant cutting and transplanting apparatus for culturing a plant tissue comprising: a plant cutting and transplantation room accommodating in a spaced-apart relationship a first culture box in which a group of multiplied plants to be cut are planted, and a second culture box in which nodular pieces made by cutting the plants are transplanted; a cutting device having a cutter adapted to cut, in one lot, the group of the plants planted in the first culture box to the form of individual nodular pieces and configured to allow the nodular pieces to rest on said cutter, said cutting device being provided in said plant cutting and transplantation room in such a way as to be moved vertically and transversely above the space where both of said first and second culture boxes are accommodated; and a blade device having a blade adapted to shake down the nodular pieces which rest on said cutter and which have been moved to a position above said second culture box for transplantation purposes.

2. A plant cutting and transplanting apparatus for culturing a plant tissue as claimed in claim 1, further comprising: a nozzle device provided in said plant cutting and transplantation room so as to spray a cleaning liquid for conducting the cutting of the plants in an aseptic condition; and a tank containing a liquid sterilizing agent and a tank containing an aseptic liquid, both of which are connected through a hydraulic pump and a change-over valve to the nozzle device.

3. A plant cutting and transplanting apparatus for culturing a plant tissue as claimed in claim 1, further comprising: a machine room located above said plant cutting and transplantation room and separated by a partition ceiling from the same; driver means installed in the machine room and adapted to drive said cutting device and said blade device; and supporting means connected to the driver means, respectively, and extending through said partition ceiling so as to support said cutter and said blade.

4. A plant cutting and transplanting apparatus for culturing a plant tissue as claimed in claim 3, characterized in that said plant cutting and transplantation room is maintained in an aseptic condition with sterile air kept at a positive pressure by ventilating air through a filter provided on said partition ceiling through the intermediary of a sealing member.

5. A plant cutting and transplanting apparatus for culturing a plant tissue as claimed in claim 3, characterized in that said blade is connected through the intermediary of a cushion member to said supporting means.

6. A plant cutting and transplanting apparatus for culturing a plant tissue comprising:
 a first culture box for maintaining therein a plurality of plants to be cut;
 a second culture box, independent of said first culture box, for accepting transplanted nodular pieces of said plants;
 first means, movable between a first position adjacent said first culture box and a second position adjacent said second culture box, for cutting said plants within said first culture box to thereby form a plurality of nodular pieces of said plants, such that said plurality of nodular pieces will rest upon said cutting means; and
 second means located adjacent said second position of said cutting means, for moving said plurality of nodular pieces from said cutting means to said second culture box for transplantation.

7. An apparatus as set forth in claim 6, further comprising means for moving said cutting means between said first and second positions.

8. An apparatus as set forth in claim 7, further comprising means for selectively moving said cutting means vertically in relation to said first cutting box so that said plurality of nodular pieces will be of a predetermined length.

* * * * *